United States Patent [19]

Frankena et al.

[11] Patent Number: 4,866,284
[45] Date of Patent: Sep. 12, 1989

[54] IRRADIATION DEVICE

[75] Inventors: Johannes A. Frankena; Jorrit Wijtsma; Marten F. Elkerbout, all of Drachten, Netherlands

[73] Assignee: U.S. Philips Corporation, New York, N.Y.

[21] Appl. No.: 154,165

[22] Filed: Feb. 8, 1988

[30] Foreign Application Priority Data

Feb. 13, 1987 [NL] Netherlands ............... 8700348

[51] Int. Cl.⁴ ............................................. G21G 4/00
[52] U.S. Cl. ................................ 250/494.1; 250/493.1
[58] Field of Search ............. 250/493.1, 494.1, 504 R; 128/396; 362/61

[56] References Cited

U.S. PATENT DOCUMENTS

| | | | |
|---|---|---|---|
| 3,084,258 | 4/1963 | Furedy | 250/494.1 |
| 3,648,706 | 3/1972 | Holzer et al. | 250/494.1 |
| 4,220,981 | 9/1980 | Koether | 362/61 |
| 4,740,707 | 4/1988 | Thaw | 250/504 R |

FOREIGN PATENT DOCUMENTS

| | | | |
|---|---|---|---|
| 3129486 | 2/1983 | Fed. Rep. of Germany | 128/396 |
| 8700257 | 1/1987 | Sweden | 250/504 R |

Primary Examiner—Bruce C. Anderson
Attorney, Agent, or Firm—Norman N. Spain

[57] ABSTRACT

Irradiation device having a base (1) which is pivotably connected by means of an arm (2) to a housing (4,5) in which radiation sources are accommodated and in which a radiation exit side is present, the housing (4,5), the arm (2) and the base (1) being collapsible to a compact unit. The housing has two juxtaposed elongated parts (4,5) accommodating radiation sources, which parts (4,5) are pivotable with respect to each other about an axis (7a, 8a) at right angles to the plane through the radiation exit side.

6 Claims, 2 Drawing Sheets

IRRADIATION DEVICE

FIELD OF THE INVENTION

The invention relates to an irradiation device having a base which is pivotably connected by means of an arm to a housing in which radiation sources are accommodated and in which a radiation exit side is present, the housing, the arm and the base being collapsible to a compact unit. An irradiation device of this type is known from European Patent Application No. 0,106,395 laid open to public inspection.

BACKGROUND OF THE INVENTION

The known irradiation device for irradiating the human body with ultraviolet radiation has a housing accommodating radiation sources such as high-pressure lamps with reflectors arranged behind them. The radiation leaves the housing via the radiation exit side (which is possibly provided with a transparent plate). The housing is pivotably connected to the wheeled base via a telescopic arm. When using the device the base is placed, for example alongside a bed on which a person to be irradiated is lying. The housing is preferably placed above the body approximately halfway its feet and head. The longitudinal direction of the housing is then generally positioned in a direction perpendicular to the axis of the body. For a satisfactory irradiation of the entire body it is necessary that the said reflectors have a special shape. However, it has been found that the differences in the radiation intensity to which the different parts of the body are exposed are relatively large.

SUMMARY OF THE INVENTION

The invention has for its object to provide a compact irradiation device with which a homogeneous irradiation of the entire human body is obtained.

According to the invention an irradiation device of the type described in the opening paragraph is therefore characterized in that the housing has two juxtaposed elongated parts accommodating radiation sources, which parts are pivotable with respect to each other about an axis at right angles to the plane through the radiation exit side.

In the operating condition of the device the two parts of the housing can easily be folded out by a user. Then a homogeneous irradiation throughout the length of the body is possible. The advantage of the device according to the invention is that the dimensions of each of the parts of the housing are relatively small as compared with the housing of the known device. The number of radiation sources is the same. The two parts of the housing are preferably pivotable (for example with respect to a coupling member located between the two parts) by means of pivots about axes which are at right angles to the radiation exit side of the housing. Right angles is herein understood to mean perpendicular with a deviation of up to approximately 30° in specific embodiments. In these embodiments the construction of arm and base has been chosen to be such that the device is collapsible in a simple manner.

Each of the two parts of the housing accommodates a plurality of radiation sources behind which reflectors are arranged. The parts of the housing have such a shape that, in the folded state, they are accommodated in recesses in the base together with the arm which is pivotably connected to the base.

A preferred embodiment of the irradiation device according to the invention is characterized in that the said parts are pivotable up to a position in which their longitudinal axes are in alignment.

The advantage of such an embodiment is that if the base of the irradiation device is placed alongside a bed, the housing above this bed assumes such a position that an optimum homogeneous irradiation of a person lying on the bed is obtained throughout the length of his body. The two parts are actually each pivotable through 90° with respect to their initial position. The device then has a stable position. The pivotal points are preferably in the form of pivots with known arresting means being provided.

In a further embodiment of the device the two parts of the housing are pivotably secured to one end of an intermediate arm whose other end is connected to the arm secured to the base.

The latter arm is preferably in the form of a telescopic arm. The said intermediate arm is in turn also pivotably secured to the telescopic arm. The housing can then easily be placed over a person to be irradiated.

The intermediate arm is preferably provided with a coupling member to which the two parts of the housing are pivotably secured. The device is then more easily collapsible. This is notably the case if the intermediate arm (which connects the two parts of the housing to the said telescopic arm) is in the form of a combination of two elongated parallel bars whose ends remote front housing are pivotably connected to a short pivotal bar which is pivotably secured to the top of the arm connected to the base. In a special embodiment this bar is bridged by a gas spring whose ends are pivotably secured to the arm and one of the parallel bars, respectively. The forces on the arm, the pivotal bar and the elongated bars are absorbed by means of the gas spring.

BRIEF DESCRIPTION OF THE DRAWING

The invention will be described in greater detail with reference to the accompanying drawings in which.

DETAILED DESCRIPTION OF THE PREFERRED EMBODIMENT

Figure 1:
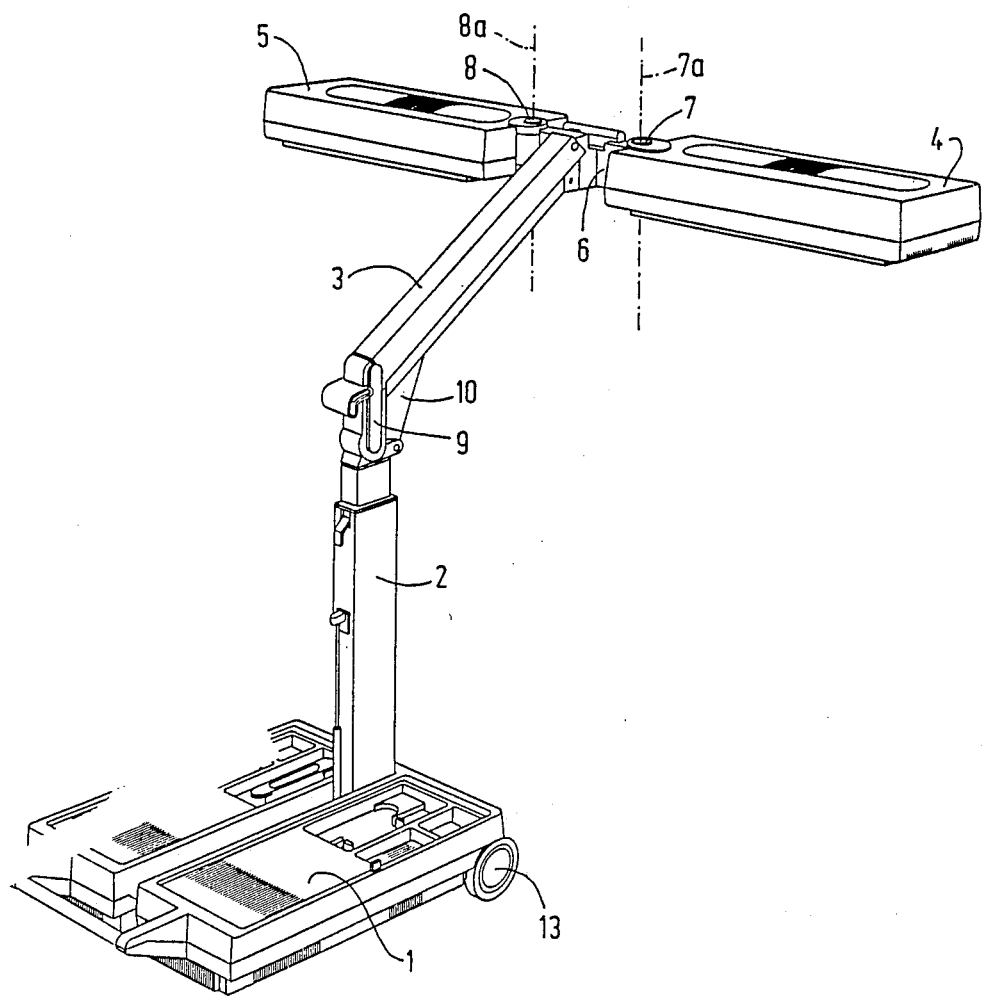
FIG. 1 is an elevational view of the irradiation device according to the invention in an operating condition.

The irradiation device of FIG. 1 has a base 1 which is connected to a housing via pivots by means of a telescopic arm 2 and an intermediate arm 3 connected thereto. This housing consists of two elongated parts 4 and 5 which are juxtaposed in a folded state. These parts 4 and 5 accommodate radiation sources (such as high-pressure mercury vapour discharge lamps in which also cobalt and iron are present in the discharge vessel) with reflectors arranged behind them. In a practical embodiment there are provided two radiation sources per part. A radiation exit side is formed on the side of the two parts facing the base. If the two parts 4 and 5 are placed side by side, the entire system can be collapsed to a compact unit. The said parts 4 and 5 are pivotable with respect to each other about an axis perpendicular to the plane through the radiation exit side (the "horizontal" plane). This is realized by providing the end of the intermediate arm 3 (which is in the form of two elongated parallel metal bars 3a and 3b, see FIG. 2) with a coupling member 6 to which the parts 4 and 5 are secured by means of pivots 7 and 8. The longitudinal axes 7a, 8a of these pivots are perpendicular to the plane through the radiation exit side of the parts 4 and 5. The other end of the intermediate arm 3 is pivotably connected to a short pivotal bar 9 secured to the top of the telescopic arm 2. This metal short pivotal bar is bridged by a gas spring 10 whose ends are also pivotably connected to the telescopic arm 2 and the intermediate arm 3, respectively.

Figure 2:
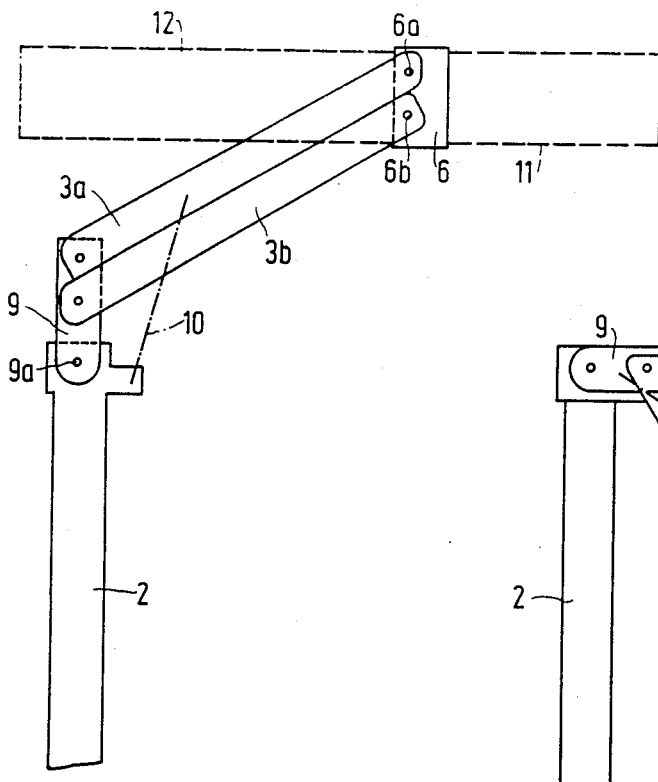
FIG. 2 is a diagrammatic longitudinal section of the device in this condition.

FIG. 2 shows the irradiation device in the operating condition. The position of the housing is indicated by broken lines. The reference numeral 11 shows diagrammatically that the longitudinal axis of each part is perpendicular to the plane of the drawing. In the position 12 the longitudinal axis is in the plane of the drawing. The parts 4 and 5 are collapsed in this position and are located side by side. The gas spring 10 is shown diagrammatically. It is connected at one end in a position near the end of the telescopic arm and at the other end to the bar 3a. The bars 3a and 3b are pivotably secured to the short pivotal bar 9 which itself is pivotable with respect to arm 2 by means of a pivot (9a). The coupling member 6 is also connected to the ends of the bars 3a and 3b by means of pivots (6a, 6b). The gas spring 10 absorbs three pivotal movements, namely that of the short pivotal bar 9 with respect to arm 2, that of bars 3a and 3b with respect to bar 9 and that of the arm 2 with respect to the bars 3a and 3b.

Figure 3:
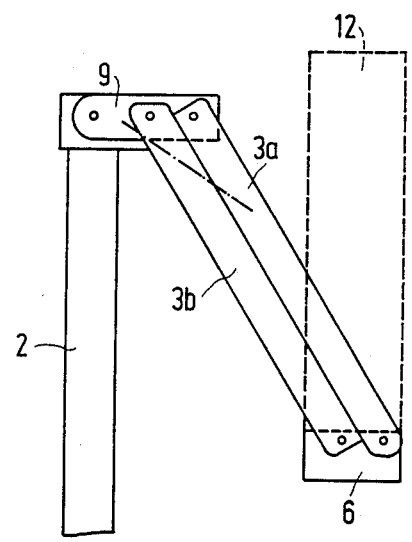
FIG. 3 also shows diagrammatically the device in a semicollapsed state.

FIG. 3 shows the irradiation device in a semi-collapsed state. The longitudinal direction of the juxtaposed parts 4 and 5 is shown in a broken line (12).

Figure 4:
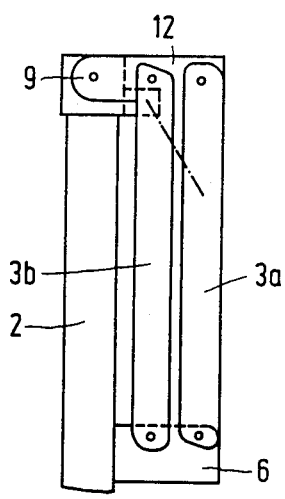
FIG. 4 shows diagrammatically the device in the fully collapsed state.

Finally FIG. 4 shows the device in the fully collapsed state. By lowering arm 2 into the base 1 (via a pivot) a compact unit is obtained with member 6 being locked with the arm 2. The base 1 accommodates the electric ballasts of the lamps. The base has also wheels (such as 13, see FIG. 1). Due to the gas spring the device immediately assumes the position as shown in FIG. 3 when the said lock is released.

In the operating condition of the irradiation device the synthetic material parts of the housing accommodate high-pressure mercury vapour discharge lamps with a power of 400 W. In addition to 20 mg of mercury the discharge vessel of such a lamp also comprises 0.16 mg of cobalt and 0.3 mg of iron. Such lamps mainly emit UV-A radiation (315–400 nm) and some UV-B radiation (280–315 nm) in addition to infrared radiation. When folding out the parts of the housing (dimensions of each part 25×15×60 cm) an irradiation field is obtained which is amply sufficient for irradiating the entire human body.

What is claimed is:

1. An irradiation device having a base which is pivotably connected by means of an arm to a housing in which radiation sources are accommodated and in which a radiation exit side is present, the housing, the arm and the base being collapsible to a compact unit, characterized in that the housing has two juxtaposed elongated parts accommodating radiation sources, which parts are pivotable with respect to each other about an axis at right angles to the plane through the radiation exit side and at right angles to the plane of said base when the planes through said base and through the radiation exit side are in parallel.

2. An irradiation device as claimed in claim 1, characterized in that the two parts are pivotable up to a position in which their longitudinal axes are in alignment.

3. An irradiation device as claimed in claim 1 or 2, characterized in that the two parts of the housing are pivotably secured to one end of an intermediate arm whose other end is connected to the arm secured to the base.

4. An irradiation device as claimed in claim 3, characterized in that one end of the intermediate arm is provided with a coupling member to which the two parts of the housing are pivotably secured.

5. An irradiation device as claimed in claim 3, characterized in that the intermediate arm is in the form of a combination of two elongated parallel bars whose ends remote from the parts of the housing are pivotably connected to a short pivotal bar which is pivotably secured to the top of the arm.

6. An irradiation device as claimed in claim 5, characterized in that the short pivotal bar is bridged by a gas spring whose ends are pivotably secured to the arm secured to the base and one of the parallel bars, respectively.

* * * * *